United States Patent [19]

Buchalter

[11] 3,989,050

[45] Nov. 2, 1976

[54] PROCESS FOR UTILIZING CERTAIN GEL COMPOSITIONS FOR ELECTRICAL STIMULATION

[76] Inventor: Gilbert Buchalter, 701 Stuyvesant Ave., Irvington, N.J. 07111

[22] Filed: Sept. 19, 1972

[21] Appl. No.: 290,402

Related U.S. Application Data

[62] Division of Ser. No. 76,610, Sept. 29, 1970, abandoned.

[52] U.S. Cl. .............................. 128/419 R; 128/417
[51] Int. Cl.² ................................................ A61N 1/36
[58] Field of Search ............... 128/172.1, 404, 405, 128/417, 418, 419 R, DIG. 4, 2.06 C; 252/500, 316; 106/169, 170, 197 C

[56] References Cited
UNITED STATES PATENTS

| | | | |
|---|---|---|---|
| 1,123,683 | 1/1915 | Clague | 128/419 R |
| 3,029,820 | 4/1962 | Franklin | 128/DIG. 4 |
| 3,163,166 | 12/1964 | Brant et al. | 128/405 |
| 3,467,863 | 9/1969 | Karsh | 128/417 |
| 3,528,408 | 9/1970 | Opperman | 128/DIG. 4 |

*Primary Examiner*—William E. Kamm

[57] ABSTRACT

A process for utilizing gel compositions containing thickening agents which are primarily long chain organic powders in combination with small amounts of auxiliary polar thickeners having no metallic cations are described. They are particularly suitable for use as electrode gels in applications where long term contact of the electrodes with the skin is necessary. The process utilizing the described gel compositions, unlike the gels known to the art will not irritate the skin, corrode the electrodes, dry out in only a few hours or leak out from the electrode.

3 Claims, No Drawings

PROCESS FOR UTILIZING CERTAIN GEL COMPOSITIONS FOR ELECTRICAL STIMULATION

This is a division of application Ser. No. 76,610 filed Sept. 29, 1970, now abandoned.

CROSS-REFERENCES

This application is not a continuation-in-part of any earlier filed application by the inventor. However, it is an important improvement of application Ser. No. 165,670 filed Jan. 11, 1962 now abandoned of which a continuation Ser. No. 798,576 filed Feb. 3, 1969 now abandoned was filed in the U.S. Patent Office in the name of the present applicant's brother, i.e. A. Herbert Buchalter.

BACKGROUND OF THE INVENTION

Electrical stimulation for medical therapy and physical rehabilitation is a very old and well established technique. Basically, it relies upon electrical impulses applied through two separate electrodes. The technique was first described as early as 1801 for use in certain paralytic conditions, palsys and neurotic conditions.

The application of amperage in varying quantities can produce considerable differences in the muscular action generated by the electrical current. Since the skin has a resistance, the currents generated by the electrodes act as a considerable irritant on the skin. It is well-established that it is necessary to use a covering on the electrode particularly if the galvanic action is intended for the deeper tissues. Now it is accepted practice, that unless a definite type of action is desired from a bare metal electrode, such as an electrolysis or metallic ionization, a galvanic current should be applied only with covered electrodes. This avoids the very painful irritation and burns which will surely result if even a moderately intense current is employed with bare electrodes.

For medical uses of electric currents for various therapeutic applications, bare metal electrodes cannot be used on the surface of the body. Thus, it has been always observed that when such electrodes have been used there results an inevitable electrolytic decomposition which occurs under the metal. Moreover, there is a considerable burn risk which is caused by acid, caustic or electrical action.

If it is essential that low-tension currents be used, then the metal elctrodes are conventionally covered with gauze or other absorbent material in sufficient width to overlap the edges of the metal. These pads are used for galvanic faradic-sinusoidal treatments. The pad on these electrodes is usually soaked with a saline solution which serves to soften the skin and ease the current.

It also diffuses the electrolytic decomposition products and tends to prevent chemical burns.

The burns caused by improper contact with too thinly coated metal electrodes or bare metal electrodes can be quite severe resulting in blisters which in turn lead to secondary infection which are very painful and heal slowly.

One of the more important areas which is amenable to treatment by the critical use of electrical stimulation is that involving denervated muscle. The stimulation retards the progression of atrophy. Furthermore, it may be necessary to have several stimulation sessions a day to retard the atrophy.

This desirably would be facilitated if the electrodes stay in contact with the afflicted area for a long period of time without constant removal or reimplacement. Even those electrode contact media which are presently commercially available do not permit the use of bare electrodes. They must be used in combination with the gauze covering of the electrode. Furthermore, the gels which are commercially available suffer the sever disadvantage that they very quickly liquefy under the influence of the ingredients in human perspiration.

An area in which the burned skin problem is particularly acute in utilizing the technology of the prior art is that of electro-shock thereapy and the defibrillation of hearts.

BRIEF SUMMARY OF THE INVENTION

It has been discovered and forms the substance of this invention that clear sparkling gels having a viscosity similar to mayonnaise can be prepared which are suitable for use for a variety of applications and particularly as electrode gels. These novel gels will not degrade on the skin into gels of a lower viscosity when exposed to the effect of perspiration. Moreover, the gel compositions of the invention permit the use of bare metal electrodes for a wide variety of electrical, therapeutic uses. No other gels known to the art permit the use of bare electrodes for such purposes. It is customary in the art to use covered electrodes.

DETAILED DESCRIPTION WITH PREFERRED EMBODIMENTS

The gel compositions of this invention exhibit outstanding properties and use for the first time the unique and inventive discovery that a particular combination of thickening agents in proper proportions results in a gel which is resistant to the effect of body perspiration.

In general, the major constituent of the combination of thickeners in any of a class of long chain ionic organic polymers which are conventionally known as good thickeners and are water soluble and have outstanding gel properties. Suitable examples include the Ganatrez materials sold by General Aniline and Film Corporation, Carbopols sold by the B. F. Goodrich Co., sodium alginate, gum tragacanth, locust bean gum, polyethylene oxide, sodium carboxymethyl cellulose, guar gum, methyl cellulose and the like.

the auxiliary thickener is any of a class in which there is an under soluble polymer with a long chain cellulosic backbone having at least one primary hydroxy group attached to each repeating cellulose molecule. These are non-ionic polymers. Generally the auxiliary thickening polymers have a Brookfield viscosity at a 1 wt. % solution viscosity (25%C. with Spindle No. 4) of from 100 to 10,000, preferably 250 to 5,000 and most preferably 1,000 to 4,000. Examples would include hydroxy methyl cellulose, methyl cellulose, hydroxy propyl cellulose. The length of the alkyl group is not significant and will usually range from 1 to 10, preferably 1 to 7 and most preferably 1 to 5. However, it is important that the thickerner used have no metallic. cation constituent.

The especially preferred gels of this invention which exhibit outstanding electrode gel properties consist of a thickener combination of carboxy polymethylene polymer and hydroxy ethyl cellulose polymer used in combination as a thickener for a water glycol mixture.

Generally, the concentration of the major thickener in the gel is about 1/20th of 1% to 10%, preferably ¼ of 1% to 5% and most preferably 0.75% to 1.6%. (Unless otherwise indicated, all weights in the application are weight percents).

The concentration of the auxiliary thickening agent in the gel formulation is generally from 1/1000 of 1% to 3%, preferably 1/100 of 1% to 1% and most preferably about 1/20 of 1% to 1/3 of 1%.

Directionally the auxiliary thickening agent should be of the highest molecular weight possible without being insoluble in the water-glycol mixture.

The pH of the gel will range from between 3-½ to 11-½, preferably 5 to 9-½ and most preferably 6 to 7.5. As a general rule of thumb the pH of the gel composition, if it is to be used as an electrode gel, will be adjusted to be as close to the pH of the human skin as possible.

In general the major thickening agent component of the invention will have a molecular weight (Staudinger) of from 30,000 to 2,000,000 preferably 60,000 to 500,000 and even more preferably 100,000 to 300,000. It is somewhat difficult to establish an absolute value for an upper limit of the degree of polymerization above which the thickening agents no longer function as efficient thickeners.

The fact is that practical considerations appear to be a primary determining factor as to the major thickener polymers and their molecular weights which can be used for the purpose of the invention. Very generally speaking, the higher the molecular weight of the major thickener polymeric material the more preferred it is for the purposes of thickening. But this is to be treated in consideration of the other factor that polar groups must also be present in the polymer to allow it to be useable in water gels. Since the water solubility of a polymer generally decreases when the molecular weight increases, one would think that this would not be a desirable property.

Nevertheless, the major thickener polymers of the invention are really members of the broad class of polyelectrolyte polymers. These do not lose water solubility as their molecular weight increases unless they become crosslinked.

It is very difficult to determine the molecular weights of very high molecular weight polymeric compounds. The figures obtained will generally vary widely depending upon the method used to determine them. It is widely recognized, for example, that molecular weights for polymeric materials which have been furnished by manufacturers usually constitute an average of the molecular weights of the molecules present.

Among the various methods used to measure molecular weights of polymeric compounds there can be included osmometrig n-group, cryoscopic, ebullioscopic, light scattering, specific viscosity, intrinsic viscosity and ultra centrifuge. Each of these methods is in various degrees of development and each one has special type of polymeric compounds to which it is especially adapted.

viscosity is a property which is much more frequently used by the polymer chemist as characterizing polymeric compounds than are molecular weights. This is no doubt due to the comparatively easier and less complicated methods for obtaining viscosity data. There is a recognized correlation between the viscosity of polymeric compounds and their relative molecular weights and since such figures can be more meaningful and can frequently be more available then molecular weights, the polymeric thickeners described in this invention are characterized in terms of viscosity where possible. Thus, the viscosities of the major thickening agents which can be used in the invention vary from a Brookfield Viscosity (CPS — centipoises per second) (20 rpm) of approximately 1000 to 100,000 at 1 wt. % aqueous concentration, preferably 15,000 to 90,000 and most preferably 18,000 to 80,000.

These viscosities are given in terms of polymeric thickeners which have been neutralized to a pH of 7.

A particularly preferred major thickening agent is a series of thickeners of water-soluble resins sold by the B. F. Goodrich Company under the tradename of Carbopol. This is a carboxy vinyl polymer, i.e. carboxy polymethylene which is essentially a vinyl polymer with active carboxylic groups. It is highly ionic and slightly acidic. Any one of the Carbopol series such as 934, 940, and 941 can be used.

The particularly preferred auxiliary thickener is a hydrozy ethyl cellulose. This is obtainable as a Cellosize from the Union Carbide Company. The Methocels from Dow Chemical are also suitable auxiliary thickening agents.

Another inventive feature of the gel particularly the preferred gel compositions of the present invention involve the use of the particular humectant. The humectants are preferably alkylene glycols wherein the alkylene groups comprises from 2 to 10 carbon atoms, preferably from 2 to 5 carbon atoms. Propylene glycol is conventionally an electrode gel component. In the electrode gels of the present invention a slight excess of propylene glycol has been added and in turn the normal preservative ingredients methyl paraben and propyl paraben have been omitted.

Generally from 10 to 25, preferably 14 to 20 and most preferably 16 to 18.5 wt. % of humectant component is included in the composition.

Not only does the use of extra glycol result in the distinct advantage of eliminating a more expensive component but it also results in the additional advantage that perfumes need not be added to the gel product. This is because the conventionally used methyl and propyl paraben components are unpleasant and must be masked with a perfume.

Thus, the propylene glycol or ingredient serves a multifaceted purpose. It is a humectant and therefore it retards drying time. It permits the elimination of auxiliary preservative and it is also a wetting or solubilizing agent due to its polyhydric alcohol characteristics.

This permits extraordinarily good wetting, solubilizing and penetrating effect when used on the skin. Therefore, as a consequence, whatever oil-interface barriers are set up between the electrode and the skin, a composition such as propylene glycol tends to lower the total electrical resistance because of its ability to wet, solubilize and penetrate the innerface.

Of course, as mentioned above the mono-, bi-, and trivalent salts are progressively bad actors in human perspiration. They are known to cause degradation of electrode gels. This results in a liquification phenomenon which results in conventional gels thinning out and becoming entirely ineffective for their purpose. The use of the auxiliary thickening agents is absolutely effective in preventing this liquification.

Generally speaking, the preparation of the gel involves the dispersion of all the thickening and humectant ingredients of the gel as well as the trace ingredients such as dye in about half the total water which is needed.

All the ingredients are then dispersed with high speed mixing using a mixer such as the Lightning line of mixers obtainable from the Mixing Equipment Corp. It is possible to use moderate speed mixing but that is less preferable because it is less efficient. Subsequently, the balance of the water is added less any water which is needed for the neutralizing agent. The mixture is allowed to stabilize and an alkaline solution is added to the mixture slowly. The pH is adjusted as described above.

A wide variety of alkaline materials can be used for neutralization. Suitable examples include amines, ethanol amines, alkali metal hydroxides, and ammonium hydroxide. Sodium and potassium hydroxides are preferred and potassium hydroxides are particularly preferred, because they impart better electrode properties to the resultant gel compositions.

It will be noted in the foregoing general description that no inorganic salts are added to the gel composition. In many of the gels which are known to the prior art, an inorganic salt is a common ingredient for the purposes of electrical conduction. This salt is probably the primary cause of skin irritation. It is theorized that this is brought about by the electrode corrosion products which result from the action of the salt on the metallic electrode.

The gel of the invention has a low polarization potential. Indeed, in actual use it appears to be essentially non-polarizing.

The preferred product of the invention having a careful balance of thickening agent, auxiliary thickening agent and humectant has a unique penetrating action which gives it a total lower resistance between the skin, the gel and the electrode then any competitive products with only surface liquification.

It also exhibits a characteristic wherein its resistance off the skin is higher than competitive products but in actual use of the skin it is much lower.

The gel composition of the invention can be used for long term monitoring where intensive care is needed such as in a situation where electrodes are placed on the patient and may remain for many hours, even weeks.

The invention is further illustrated by the following Examples.

EXAMPLE I

Compositions of the prior art and those of the present invention having the following formulations were prepared for comparison purposes. (All precentages are weight percents unless otherwise indicated).

|  | Prior Art | Present Invention |
|---|---|---|
| Carboxy Polymethylene (Carbopol 934)(1) | .6 % | 1 % |
| Hydroxy Ethyl Cellulose (QP 100M)(2) | — | 1/6 of 1 % |
| Propylene Glycol | 16 % | 18 % |
| Methyl Paraben | .18T | — |
| Propyl Paraben | .03 % | — |
| Perfume | .004 % | — |
| F.D. & C. Color | .001 % | .001 % |
| Sodium Hydroxide | .39 % of Carbopol | — |
| Potassium Hydroxide | — | 0.55 % of Carbopol |
| Water | Balance to | Balance to 100 % |

-continued

|  | Prior Art | Present Invention |
|---|---|---|
|  |  | 100 % |

(1)This is a white powder which has a Brookfield RVF or RVJ 20 rpm No. spindle at 25° C. ± 0.5° C. for an 0.2 % neutralized solution of from 2,050 to 5,450.
(2)obtainable as Cellosize HEC from Union Carbide
QP = quick processing. A non-ionic water-soluble cellulose ether with a solution viscosity at 1 wt. % in $H_2O$ of 2,500 to 3,000 CPS. This is Brookfield Viscosity at 25° C. with Spindle No. 4.

The above described prior art composition was prepared as follows:

The preservatives (methyl and propyl paraben) were dissolved in the propylene glycol. The Perfume was then dispersed. One half of the total volume of water was then added. The Carbopol 934 was dispersed with high speed mixing. The dye was then added.

The balance of the water was added, less the water needed for dissolving the alkali metal.

This total mixture was allowed to stand, without further agitation, for several days for the air bubbles to disperse.

Upon completion of this stabilizing time, the alkali metal hydroxide was dissolved in the proper amount of water and added to the above mixture with slow agitation until the gel was formed and was completely uniform.

The physical characteristics of the mixture prior to neutralization with alkali metal hydroxide were a thin, pourable, milky liquid approximately the viscosity of light cream.

The physical characteristics upon completion of neutralization was a clear, sparkling gel with a viscosity similar to that of mayonnaise or sour cream. That is to say, the product would not pour or run unless it was under pressure (squeezed out of a plastic container).

The major differences in the formulation of the gel composition of the invention in contrast to the prior art gel are:

The methyl and propyl paraben were completely eliminated, as research indicated the increased percentage of propylene glycol in itself was sufficient for preservation.

The hydroxy ethyl cellulose (HEC) was dispersed simultaneously with the Carbopol 934.

This resulted in a thicker or higher viscosity preneutralized liquid as the thickening ability of HEC is not dependent upon pH.

Neutralization was effected with potassium hydroxide as the alkali metal hydroxide in contrast to sodium hydroxide as the potassium ion is a better electrical conductor than sodium (it is a poor ultrasound conductor).

The elimination of the methyl and propyl paraben as preservatives allowed the creation of a totally odorless product which did not require the necessity of perfume to mask the preservative odor.

The propylene glycol content of the novel gel composition is higher than that of the prior art gel because in the novel gel composition, it is used for three different and distinct purposes.

In the prior art gel it is used solely for the retarding of drying time as it is a humectant.

It is used in the novel gel composition for this purpose; in fact, the concentration is higher as it is desirable that the drying time be prolonged.

This higher concentration enabled it to be used as the sole preservative in the composition.

It also has the advantage of being a wetting or solubilizing agent due to the fact that it is an alcohol.

This wetting, solubilizing and penetrating effect is responsible for lowering the total electrical resistance when in use, as it tends to wet, solubilize and penetrate the oilskin barrier.

EXAMPLE II

Tests were performed which have proven that using the novel gel composition for regular electrocardiogram monitoring allows the use of either a pediatric electrode, or a specially modified electrode (original tests were done using a penny and a lightweight shielded cable insteand of the cumbersome and costly suction cup chest electrodes and the strap electrodes for the arm or leg.

The high viscosity of the novel gel composition held the small electrode (pediatric or penny) in place without the necessity of mechanical assistance from the suction cup or straps resulting in a saving of time and cost.

EXAMPLE III

The basic technique for stimulation of denervated muscles with direct current was used. The dispersive pad electrode was thoroughly saturated with warm water and placed outside the area being treated — in all cases the hand on the affected side was used to complete the circuit.

The felt and asbestos covering was removed from a conventional "diagnostic" tap key electrode. The stainless steel electrode plate used was 2 cm. in diameter. The dispersive electrode was left intact with its commercial covering over the plate. A single sheet of paper toweling cut to size was used over the dispersive pad as a sanitary measure.

The electrode gel composition of the invention described in Example 1 was applied to the active electrode, and to the motor point areas in a 0.5 cm thick glob. A direct current was used for stimulation — interrupted by means of a make and break technique with the tap key electrode. Care was taken to apply minimal pressure on the tap key electrode. Too much pressure on the electrode caused a mechanical removal of the gel, resulting in patient discomfort and diminished response.

Following completion of the treatment, the gel was removed from the skin with a tissue. The active electrode was rinsed under hot water and placed in a cold sterilization pan.

A group of five volunteers was used to determine the comfort level as well as skin sensitivity of the technique. The motor points of the face were used as the testing site due to the inherent sensitivity of the face. A conventional electrode was also used with the usually recommended media on the volunteer subjects to provide a basis for comparison of intensity required for good muscle contractions.

Following the trial period with the volunteer subjects, five patients, one male and four female, ranging in age from forty-four to sivty-five were treated with the new technique outlined. Pathologies included: Bell's Palsy 3; Ramsay Hart Syndrome 1; Diabetic neuropathy 1.

A total of 132 treatments were given. Frequency of treatment ranged from once daily to once weekly. Four of the five patients received electrical stimulation to the face. The fifth patient, a female, received stimulation to the anterior tibialis for treatment of a diabetic neuropathy. All muscles stimulated were denervated by the course of the specific pathologies.

The use of the aqueous gel composition of the invention facilitated placement and permitted a sliding movement of the electrode on the skin; thus minute relocations of the electrode were possible without losing skin contact while the optimal response point was being determined.

The viscosity of the gel provided constant contact even over hairy areas and structural contours which are usually problem areas. This continuous rather than interrupted contact of the electrode provided a new level of patient comfort. Patient comfort level was also improved through the reduction of intensity and local sensation of heat. The cool skin sensation experienced by the patient diminishes his anxiety regarding burn.

The use of sanitary covering such as gauze, paper and the like over the conventional electrodes, are at best a false security. Since water or media solution necessarily passes through these "sanitary" coverings, which are not bacterial filters, the bacteria has a free avenue of flow from the electrode covering to the patient. This great potential hazard of cross infection can be eliminated by using the bare electrode as described. The bare electrode which can be sterilized, has no areas for bacteria to collect, grow and cause cross contamination. Further, there is no time lost wrapping the electrodes as a "protective" measure.

Basically, the use of the gel composition of the invention provides an entirely new process technique to the art for electrical stimulation using bare electrodes.

Thus, for the first time with galvanic currents, it was possible to obtain good muscle contractions with low intensity current, electrode sterilization was readily obtainable, good skin contact was facilitated and cutaneous hyperemia and erythemia was absent.

What is claimed is:

1. The process of electrical stimulation which comprises the steps of:
  a. applying a perspiration-resistant gel composition comprising a major proportion of water
  from 1/20th of 1 wt. % to 10 wt. % of a long chain water soluble ionic polymeric thickener having a Brookfield viscosity (CPS) of approximately 1,000 to 100,000 at a 1 wt. % concentration in $H_2O$, which has been neutralized with an alkali metal hydroxide,
  from 1/1,000 of 1 wt. % to 3 wt. % of a cellulosic backbone auxiliary thickener having no metallic ion constituent which has at least one primary hydroxy group attached to each repeating unit in the cellulose backbone having a 1 wt. % solution viscosity (Brookfield) at 25° C. of from 100 to 10,000 and
  from 10.5 to 25 wt. % of a polyol humectant wherein said gel has a pH of between 3.5 to 11.5, to the surface of an animal, including humans,
  b. firmly contacting the resulting gel area with at least one metal electrode,
  c. applying a galvanic force between said electrode and said surface.

2. The process of claim 1 wherein said gel composition contains sodium hydroxide or potassium hydroxide, said polymeric thickener is chosen from the group consisting of Ganatrez, sodium alginate, gum tragacanth, locust bean gum, polyethylene oxide, sodium carboxymethyl cellulose, guar gum, methyl cellulose, Carbopol and mixtures thereof, said auxiliary thickener is a hydroxy alkylene cellulose polymer, and said humectant is a polyalkylene glycol wherein said alkylene groups comprise from 2 to 10 carbon atoms.

3. The process of claim 1 wherein said gel contains as said polymeric thickener, Carbopol; and as said auxiliary thickener, hydroxy ethyl cellulose; and as said humectant, propylene glycol.

* * * * *